US005618530A

United States Patent [19]

Mandeville, III et al.

[11] Patent Number: 5,618,530

[45] Date of Patent: Apr. 8, 1997

[54] HYDROPHOBIC AMINE POLYMER SEQUESTRANT AND METHOD OF CHOLESTEROL DEPLETION

[75] Inventors: W. Harry Mandeville, III, Lynnfield; Stephen R. Holmes-Farley, Arlington; John S. Petersen, Acton, all of Mass.

[73] Assignee: GelTex Pharmaceuticals, Inc., Waltham, Mass.

[21] Appl. No.: 469,659

[22] Filed: Jun. 6, 1995

Related U.S. Application Data

[63] Continuation-in-part of Ser. No. 258,431, Jun. 10, 1994, and Ser. No. 332,096, Oct. 31, 1994.

[51] Int. Cl.$^6$ ................................................. A61K 31/785
[52] U.S. Cl. ................................ 424/78.12; 424/78.27
[58] Field of Search ................................ 424/78.12, 486, 424/497, 78.27; 514/824; 525/328.2, 379

[56]  References Cited

U.S. PATENT DOCUMENTS

| | | | |
|---|---|---|---|
| 3,288,770 | 11/1966 | Butler | 260/88.3 |
| 3,308,020 | 3/1967 | Wolf et al. | 167/65 |
| 3,383,281 | 5/1968 | Wolf et al. | 167/65 |
| 3,692,895 | 9/1972 | Nelson et al. | 424/78 |
| 3,780,171 | 12/1973 | Irmscher et al. | 424/79 |
| 3,787,474 | 1/1974 | Daniels et al. | 260/459 |
| 3,803,237 | 4/1974 | Lednicer et al. | 260/584 R |
| 3,980,770 | 9/1976 | Ingelman et al. | 424/79 |
| 4,027,009 | 5/1977 | Grier et al. | 424/78 |
| 4,071,478 | 1/1978 | Shen et al. | 260/2 R |
| 4,098,726 | 7/1978 | Wagner et al. | 528/403 |
| 4,101,461 | 7/1978 | Strop et al. | 521/32 |
| 4,111,859 | 9/1978 | Strop et al. | 521/33 |
| 4,205,064 | 5/1980 | Wagner et al. | 424/78 |
| 4,217,429 | 8/1980 | Wagner et al. | 525/411 |
| 4,340,585 | 7/1982 | Borzatta et al. | 424/79 |
| 4,540,760 | 9/1985 | Harada et al. | 526/211 |
| 4,557,930 | 12/1985 | Kihara et al. | 424/79 |
| 4,559,391 | 12/1985 | Ueda et al. | 525/366 |
| 4,605,701 | 8/1986 | Harada et al. | 525/107 |
| 4,680,360 | 7/1987 | Ueda et al. | 526/310 |
| 4,759,923 | 7/1988 | Buntin et al. | 424/440 |
| 5,055,197 | 10/1991 | Albright et al. | 210/638 |
| 5,236,701 | 8/1993 | St. Pierre et al. | 424/78 |
| 5,374,422 | 12/1994 | St. Pierre et al. | 424/78.12 |
| 5,430,110 | 7/1995 | Ahlers et al. | 525/328.2 |
| 5,451,397 | 9/1995 | Albright et al. | 424/78.01 |
| 5,462,730 | 10/1995 | McTaggart et al. | 424/78.35 |

FOREIGN PATENT DOCUMENTS

| | | |
|---|---|---|
| 0162388 | 11/1985 | European Pat. Off. . |
| 0373852A2 | 6/1990 | European Pat. Off. . |
| 0432995A1 | 6/1991 | European Pat. Off. . |
| 0459632A1 | 12/1991 | European Pat. Off. . |
| 929391 | 6/1963 | United Kingdom . |
| 1567294 | 5/1980 | United Kingdom . |
| WO91/18027 | 11/1991 | WIPO . |
| WO92/10522 | 6/1992 | WIPO . |
| WO94/04596 | 3/1994 | WIPO . |
| WO94/27620 | 12/1994 | WIPO . |

OTHER PUBLICATIONS

Heming, A.E. and Flanagan, Thomas L., "Considerations in the Selection of Cation Exchange Resins for Therapeutic Use," *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

*Primary Examiner*—Charles T. Jordan
*Assistant Examiner*—John R. Hardee
*Attorney, Agent, or Firm*—Hamilton, Brook, Smith & Reynolds, P.C.

[57]  ABSTRACT

An amine polymer includes a substituent bound to an amine of the polymer. The substituent includes a quaternary amine-containing moiety having at least one hydrophobic moiety. A method for binding bile salts of bile acids in a mammal includes orally administering to the mammal a therapeutically-effective amount of the amine polymer.

17 Claims, No Drawings

5,618,530

HYDROPHOBIC AMINE POLYMER SEQUESTRANT AND METHOD OF CHOLESTEROL DEPLETION

RELATED APPLICATIONS

This is a continuation-in-part of application Ser. No. 08/258,431, filed Jun. 10, 1994, and of application Ser. No. 08/332,096, filed Oct. 31, 1994.

BACKGROUND OF THE INVENTION

Salts of bile acids act as detergents to solubilize and consequently aid in digestion of dietary fats. Bile acids are precursors to bile salts, and are derived from cholesterol. Following digestion, bile acids can be passively absorbed in the jejunum, or, in the case of conjugated primary bile acids, reabsorbed by active transport in the ileum. Bile acids which are not reabsorbed are deconjugated and dehydroxylated by bacterial action in the distal ileum and large intestine.

Reabsorption of bile acids from the intestine conserves lipoprotein cholesterol in the bloodstream. Conversely, blood cholesterol level can be diminished by reducing reabsorption of bile acids.

One method of reducing the amount of bile acids that are reabsorbed is oral administration of compounds that sequester the bile acids and cannot themselves be absorbed. The sequestered bile acids are consequently excreted.

Many bile acid sequestrants, however, do not bind conjugated primary bile acids, such as conjugated cholic and chenodeoxycholic acids well enough to prevent substantial portions from being reabsorbed. In addition, the volume of sequestrants that can be ingested safely is limited. As a result, the effectiveness of sequestrants to diminish blood cholesterol levels is also limited.

A need exists, therefore, for a sequestrant and a method which overcomes or minimizes the referenced problems.

SUMMARY OF THE INVENTION

The present invention relates to amine polymer sequestrants and to a method for binding salts of bile acids in a mammal.

The amine polymer includes a substituent bound to an amine of the amine polymer, the substituent including a quaternary amine-containing moiety having at least one hydrophobic substituent.

The method includes orally administering to a mammal a therapeutic amount of an amine polymer with a substituent bound to an amine of the amine polymer, the substituent including a quaternary amine-containing moiety having a hydrophobic substituent.

This invention has many advantages. For example, the amine polymer of the invention binds conjugated primary bile acids that would otherwise be reabsorbed by active transport. Additionally, the sequestration of primary bile acids by the amine polymer is essentially irreversible in the intestine, as evidenced by the fact that bacterial deconjugation and dehydroxylation of bound bile acids is substantially prevented. Consequently, the effectiveness of a given dosage of sequestrant to diminish plasma lipid levels is significantly increased. Other, specific advantages include reduced hepatic and aortic lipid levels and enhanced antiatherosclerotic activity.

DETAILED DESCRIPTION OF THE INVENTION

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The amine polymer of the invention includes a substituent bound to an amine of the amine polymer. The substituent includes at least one hydrophobic moiety. The amine polymers of the invention are particularly suitable for binding conjugated primary bile acids, such as cholic and chenodeoxycholic acids, in mammals by oral administration of the polymer. A particularly suitable form for oral administration of the amine polymer is that which will form a gel in the stomach of a patient.

Examples of suitable methods by which the amine polymer of the invention can be formed are shown below:

1. One method involves polymerization of an amine monomer to form a homopolymer. Examples of this method include polymerization of allylamine, ethyleneimine, vinylamine, 1,2-diaminoethene, aminoethylacrylamide, aminopropylacrylate, or p-aminomethylstyrene, to form their respective homopolymers.

2. Another method involves copolymerizing an amine monomer with one or more additional monomers. These additional monomers include amine monomers, such as those listed above, and non-amine monomers, such as acrylamide, styrene, divinylbenzene, vinyl alcohol, or vinyl chloride. Examples include copoly(allylamine/acrylamide), copoly(vinylamine/allylamine), copoly(aminoethylacrylamide/acrylamide), and copoly(allylamine/divinylbenzene).

3. Still another method involves polymerization of a non-amine monomer to form a homopolymer that is subsequently chemically modified to form an amino polymer. Examples of this method include polymerization of vinyl formamide, vinyl acetamide, vinyl chloride, vinyl bromide, allyl chloride, allyl bromide, acrylamide, or acrylonitrile, to form their respective homopolymers. Each homopolymer would then be chemically altered to form an amine polymer using such reactions as hydrolysis, nucleophilic substitution, or reduction. The first four homopolymers listed above would then become poly(vinylamine) and the last four would become poly(allylamine). It is to be understood that not all of the initial non-amine monomer need be chemically altered, resulting in an amine polymer that contains some of the initial non-amine monomers in a non-amine state.

4. A fourth method involves copolymerizing a non-amine monomer with one or more additional monomers. These additional monomers could include amine monomers, such as those listed in the first method, and non-amine monomers, such as those listed in the third method. The resulting copolymer would then be chemically altered to form an amine polymer as in the third method. Examples would include copolymerization of acrylamide and styrene, followed by reduction to form copoly(allylamine/styrene), copolymerization of acrylonitrile and vinyl formamide, followed by reduction and hydrolysis, to form copoly(allylamine/vinylamine), and copolymerization of acrylonitrile and allylamine, followed by reduction, to form poly(allylamine). It is to be understood that not all of the initial non-amine monomer be chemically altered, resulting in an amine polymer that contains some of the initial non-amine monomers in a non-amine state.

5. A fifth method involves forming an amine polymer through a condensation mechanism. Examples of this method would include reaction of diethylenetriamine and epichlorohydrin, 1,3-dibromopropane and ethylenediamine, spermine and 1,4-butanediol diglycidyl ether, or tris(2-aminoethyl)amine and 1,10-dibromodecane.

Each of these amine polymers typically has a molecular weight greater than 2,000. Examples of resulting suitable amine polymers include poly(vinylamine), poly(allylamine), and poly(ethyleneimine). A preferred amine polymer is poly(allylamine).

Preferably, the amine polymer is crosslinked, such as by reacting the polymer with a suitable crosslinking agent. Examples of suitable crosslinking agents include acryloyl chloride, epichlorohydrin, butanedioldiglycidyl ether, ethanedioldiglycidyl ether, dimethyl succinate, etc. Epichlorohydrin is a preferred crosslinking agent. Typically, the amount of crosslinking agent that is reacted with the amine polymer is sufficient to cause between about 0.5 and twenty percent of the amines available for reaction to react with the crosslinking agent. In a preferred embodiment, between about 0.5 and six percent of the amine groups react with the crosslinking agent.

Crosslinking of the polymer can be achieved by reacting the polymer with a suitable crosslinking agent in an aqueous caustic solution at about 25° C. for a period of time of about eighteen hours to thereby form a gel. The gel is then combined with water or dried to form a particulate solid. The particulate solid can then be washed with water and dried under suitable conditions, such as a temperature of about 50° C. for a period of time of about eighteen hours.

The amine polymer can then be alkylated. An "alkylating agent," as that term is employed herein means a reactant that, when reacted with a crosslinked polymer, causes a substituted alkylammonium salt to be covalently bound to one or more of the nitrogen atoms of the polymer.

At least one alkylating agent is employed to react with the amine polymer to form the substituent on the amine polymer. The substituent is bound to an amine of the amine polymer, and includes a quaternary amine moiety having a hydrophobic substituent. The hydrophobic substituent does not include a linking group between the amine of the polymer and the quaternary amine. In one embodiment, the quaternary amine-containing moiety of the substituent includes an alkyl component having between about six and twenty carbons. Examples of preferred alkyl groups of the alkylating agent are hexyl, octyl, decyl and dodecyl groups. The alkylating agent can include a suitable leaving group, such as a halide, epoxy, tosylate, or mesylate group. In the case of, e.g., epoxy groups, the alkylation reaction causes opening of the three-membered epoxy ring. Particular examples of suitable alkylating agents include the following:
(3-bromopropyl)dodecyldimethylammonium bromide;
(3-bromopropyl)octyldimethylammonium bromide;
(3-iodobutyl)dioctylmethylammonium bromide;
(2,3-epoxypropyl)decyldimethylammonium bromide;
(5-tosylpentyl)dodecyldimethylammonium bromide;
(6-bromohexyl)octyldimethylammonium bromide;
(12-bromododecyl)decyldimethylammonium bromide;
(3-bromopropyl)tridecylammonium bromide;
(2-bromoethyl)docosyldimethylammonium bromide;
(3-bromopropyl)docosyldimethylammonium bromide;
(3-bromohexyl)docosyldimethylammonium bromide;
(2-bromoethyl)dodecyldimethylammonium bromide;
(2-bromoethyl)decyldimethylammonium bromide; etc.

It is to be understood that the above compounds can be employed in halogenated forms other than bromides, such as chlorides.

The amine polymer is typically alkylated by combining the polymer with the alkylating agent in an organic solvent. The amount of the alkylating agent combined with the amine polymer is generally sufficient to cause reaction of the alkylating agent with between about five and ninety-five percent of amine groups on the amine polymer. Preferably the range is between about ten and ninety-five percent. In a particularly preferred embodiment, the range is between about thirty and ninety-five percent. Examples of suitable organic solvents include methanol, ethanol, acetonitrile, etc. A preferred organic solvent is methanol.

In one embodiment, the reaction mixture is heated over a period of about forty minutes to a temperature of about 65° C., with stirring. Typically, an aqueous sodium hydroxide solution is intermittently added during the reaction period. Preferably, the reaction period at 65° C. is about eighteen hours, followed by gradual cooling to a room temperature of about 25° C. over a period of about four hours. The resulting reaction product is then filtered, resuspended in methanol, filtered again, and then washed with a suitable aqueous solution, such as two molar sodium chloride, and then with deionized water. The resultant solid product is then dried under suitable conditions, such as at a temperature of about 60° C. in a forced-air oven. The dried solid can then be subsequently processed. Preferably, the solid is ground and passed through an 80 mesh sieve.

In a particularly preferred embodiment of the invention, the amine polymer is a crosslinked poly(allylamine), wherein the substituent includes (3-bromopropyl)dodecyldimethylammonium bromide. Further, the particularly preferred crosslinked poly(allylamine) is crosslinked by epichlorohydrin that is present in a range of between about two and six percent of the amines of the polymer.

The amine polymer of the invention can be subsequently treated or combined with other materials to form a composition for oral administration of the amine polymer.

The present pharmaceutical compositions are generally prepared by known procedures using well known and readily available ingredients. In making the compositions of the present invention, the amine polymer can be present alone, can by admixed with a carrier, diluted by a carrier, or enclosed within a carrier which may be in the form of a capsule, sachet, paper or other container. When the carrier serves as a diluent, it can be a solid, semi-solid or liquid material which acts as a vehicle, excipient or medium for the polymer. Thus, the compositions can be in the form of tablets, pills, powders, lozenges, sachets, cachets, elixirs, suspensions, syrups, aerosols, (as a solid or in a liquid medium), soft or hard gelatin capsules, sterile packaged powders, and the like. Examples of suitable carrier, excipients, and diluents include foods, drinks, lactose, dextrose, sucrose, sorbitol, mannitol, starches, gum acacia, alginates, tragacanth, gelatin, calcium silicate, microcrystalline cellulose, polyvinylpyrrolidone, cellulose, methyl cellulose, methylhydroxybenzoates, propylhydroxybenzoates, propylhydroxybenzoates, and talc.

A negatively charged counterion of the pharmaceutical composition can include organic ions, inorganic ions, or combinations thereof. Inorganic ions suitable for use in this invention include halide (especially chloride), phosphate, carbonate, bicarbonate, and sulfate. Suitable organics ions include acetate, ascorbate, benzoate, citrate, dihydrogen citrate, hydrogen citrate, oxalate, succinate, and tartrate.

In a preferred embodiment, the counterion does not have a detrimental side effect to the patient but rather is selected to have a therapeutic or nutritional benefit to the patient.

The method of the invention includes administering to a mammal, such as by oral administration, a therapeutic amount of the amine polymer having a substituent bound to an amine of the amine polymer, the substituent including a quaternary amine containing moiety having a hydrophobic substituent. Generally, a therapeutic amount of the amine polymer is an amount of the amine polymer in a range of between about 0.1 grams/day and about 10 grams/day.

In one embodiment, the method of the invention is a method for binding bile salts in a mammal, comprising the step of orally administering to the mammal a therapeutic amount of the amine polymer of the invention. In another embodiment, the invention is a method for reducing blood cholesterol in a mammal, comprising the step of administering to the mammal a therapeutic amount of the amine polymer of the invention. In still another embodiment, the invention includes a method for treating atherosclerosis in a mammal, comprising the step of administering to the mammal a therapeutic amount of the amine polymer of the invention. In still another embodiment, the method of the invention is that of treating hypercholesterolemia in a mammal, comprising the step of administering to the mammal a therapeutic amount of the amine polymer of the invention.

Another embodiment of the invention is a method for reducing plasma lipid content of a mammal, comprising the step of orally administering to the mammal the amine polymer of the invention to tightly sequester conjugated primary bile acids secreted by the mammal, whereby a substantial portion of the conjugated primary bile acids are excreted by the mammal, thereby causing accelerated lipid metabolization and consequent lowering of plasma lipid content of the mammal. In a preferred embodiment, the sequestered conjugated primary bile acids include conjugated cholic acid and conjugate chenodeoxycholic acid.

It is believed that the amine polymer of the invention can bind conjugated primary bile acids, cholic and chenodeoxycholic acids, with sufficient affinity to prevent both active transport of these bile acids, and bacterial deconjugation and dehydroxylation that normally occurs in the large intestine. Further, it is believed that this high-affinity binding, which in effect removes significant portions of conjugated cholic and chenodeoxycholic acids from the jejunal and ileal bile acids pool, and can result in enhanced lipid lowering and antiatherosclerotic effects.

The teachings of U.S. patent application Ser. No. 08/471,769 entitled "Amine Polymer Sequestrant and Method of Cholesterol Depletion," filed Jun. 6, 1995, by Mandeville et al. are incorporated herein by reference in their entirety.

The invention will now be further and specifically described by the following examples. All parts and percentages are by weight unless otherwise specified.

Exemplification

Example 1

Preparation of a Poly(allylamine) Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 grams) was added dropwise with stirring while maintaining the reaction temperature at 5°–10° C. After addition was complete, the mixture was removed, placed in a 3 liter one-neck flask, and 206 grams of liquid was removed by rotary vacuum evaporation at 60° C. Water (20 mL) was then added and the liquid was returned to the reaction kettle. Azobis(amidinopropane) dihydrochloride (0.5 grams) suspended in 11 mL of water was then added. The resulting reaction mixture was heated to 50° C. under a nitrogen atmosphere with stirring for 24 hours. Additional azobis(amidinopropane) dihydrochloride (0.5 grams) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, resuspended in methanol (4 L), stirred for 1 hour, and collected by filtration. The methanol rinse was then repeated one more time and the solid dried in a vacuum oven to afford 215.1 grams of poly(allylamine) hydrochloride as a granular white solid.

Example 2

Preparation of Poly(allylamine) Hydrochloride

Crosslinked with Epichlorohydrin

To a 5 gal vessel was added poly(allylamine) hydrochloride prepared as described in Example 1 (1 kg) and water (4 L). The mixture was stirred to dissolve the hydrochloride and the pH was adjusted by adding solid NaOH (284 grams). The resulting solution was cooled to room temperature, after which epichlorohydrin crosslinking agent (50 mL) was added all at once with stirring. The resulting mixture was stirred gently until it gelled (about 35 minutes). The crosslinking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum over at 50° C. for 18 hours to yield about 677 grams of the crosslinked polymer as a granular, brittle, white solid.

Example 3

Crosslinked poly(allylamine) was made as stated in Example 2. To a flask were added the crosslinked poly(allylamine) (12.5 grams; 6% crosslinked; ground to ~30 mesh), (3-bromopropyl)dodecyldimethylammonium bromide (17.5 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (1.14 grams of 50% solution) was added and the stirring continued at 65° C. for 2 hours. Two additional aliquots of aqueous sodium hydroxide (1.14 grams of 50% solution) were sequentially added and the stirring continued at 65° C. for an additional 2 hours for each aliquot. Aqueous sodium hydroxide (1.14 grams of 50% solution) was then added and the stirring continued at 65° C. for an additional 12 hours. The mixture was then allowed to cool to room temperature.

The solid product was filtered off and washed by suspension, stirring for 30 minutes, and filtration, from the following fluids:

1. 459 mL 2 M NaCl (aqueous)
2. 459 mL 2 M NaCl (aqueous)

3. 2 L deionized water
4. 2 L deionized water
5. 2 L deionized water
6. 2 L deionized water The solid was then dried in a 60° C. forced-air oven to yield 17.4 grams of an off-white solid. The solid was then ground and passed through an 80 mesh sieve.

Example 4

Crosslinked poly(allylamine) was made as stated in Example 2. To a flask were added the crosslinked poly(allylamine) (12.5 grams; 6% crosslinked; ground to ~30 mesh), (3-bromopropyl)dodecyldimethylammonium bromide (35 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (1.99 grams of 50% solution) was added and the stirring continued at 65° C. for 2 hours. Two additional aliquots of aqueous sodium hydroxide (1.99 grams of 50% solution) were sequentially added and the stirring continued at 65° C. for an additional 2 hours for each aliquot. Aqueous sodium hydroxide (1.99 grams of 50% solution) was then added and the stirring continued at 65° C. for an additional 12 hours. The mixture was then allowed to cool to room temperature.

The solid product was filtered off and washed by suspension, stirring for 30 minutes, and filtration, from the following fluids:

1. 459 mL 2 M NaCl (aqueous)
2. 459 mL 2 M NaCl (aqueous)
3. 2 L deionized water
4. 2 L deionized water
5. 2 L deionized water
6. 2 L deionized water The solid was then dried in a 60° C. forced air drying oven to yield 25.6 grams of an off-white solid. The solid was ground and passed through an 80 mesh sieve.

Example 5

Crosslinked poly(allylamine) was produced by the method of Example 2, with the exception that 16.7 mL of epichlorohydrin was employed, rather than 50 mL. To a flask were added crosslinked poly(allylamine) (12.5 grams; 2% crosslinked; ground to ~30 mesh), (3-bromopropyl)dodecyldimethylammonium bromide (140.8 grams; made by reaction of 1,3-dibromopropane and N,N-dimethyl-1-aminododecane in diethyl ether), and methanol (334 mL). The mixture was heated to 65° C. with stirring. Upon reaching 65° C., aqueous sodium hydroxide (7.1 grams of 50% solution) was added and the stirring continued at 65° C. for 2 hours. Two additional aliquots of aqueous sodium hydroxide (7.1 grams of 50% solution) were sequentially added and the stirring continued at 65° C. for an additional 2 hours for each aliquot. Aqueous sodium hydroxide (7.1 grams of 50% solution) was added and the stirring continued at 65° C. for an additional 12 hours. The mixture was then allowed to cool to room temperature.

The solid product was filtered off and washed by suspension, stirring for 30 minutes, and filtration from the following fluids:

1. 1.7 L 2 M NaCl (aqueous)
2. 1.7 L 2 M NaCl (aqueous)
3. 8 L deionized water
4. 8 L deionized water
5. 8 L deionized water
6. 8 L deionized water
7. 4 L deionized water The solid was then dried in a 60° C. forced air drying oven to yield 39.8 grams of an off-white solid. The solid was ground and passed through an 80 mesh sieve.

Example 6

Crosslinked poly(allylamine) was made as stated in Example 2. To a flask were added crosslinked poly(allylamine) (12.5 grams; 6% crosslinked; ground to ~30 mesh), (3-bromopropyl)octyldimethylammonium bromide (30.2 grams; made by reaction of 1,3-dibromopropane and N,N-dimethyl-1-aminooctane in diethyl ether), and methanol (334 mL). The mixture was heated to 65° C. with stirring. Upon reaching 65° C.m aqueous sodium hydroxide (2.0 grams of 50% solution) was added and the stirring continued at 65° C. for hours. Two additional aliquots of aqueous sodium hydroxide (2.0 grams of 50% solution) were sequentially added and the stirring continued at 65° C. for an additional hours for each aliquot. Aqueous sodium hydroxide (2.0 grams of 50% solution) was then added and the stirring continued at 65° C. for an additional 12 hours. The mixture was then allowed to cool to room temperature. The solid product was filtered off and washed by suspension, stirring for 30 minutes, and filtration from the following fluids:

1. 800 mL 2 M NaCl (aqueous)
2. 800 mL 2 M NaCl (aqueous)
3. 2 L deionized water
4. 2 L deionized water
5. 1 L deionized water The solid was then dried in a 60° C. forced air drying oven to yield 16.8 grams of an off-white solid. The solid was ground and passed through an 80 mesh sieve.

Example 7

Crosslinked poly(allylamine) was made as stated in Example 2. To a flask were added crosslinked poly(allylamine) (12.5 grams; 6% crosslinked; ground to ~30 mesh), (6-bromohexyl)octyldimethylammonium bromide (33.7 grams; made by reaction of 1,6-dibromohexane and N,N-dimethyl-1-aminooctane in diethyl ether), and methanol (334 mL). The mixture was heated to 65° C. with stirring. Upon reaching 65° C., aqueous sodium hydroxide (1.68 grams of 50% solution) was added and the stirring continued at 65° C. for 2 hours. Two additional aliquots of aqueous sodium hydroxide (1.68 grams of 50% solution) were sequentially added and the stirring continued at 65° C. for an additional 2 hours for each aliquot. Aqueous sodium hydroxide (1.68 grams of 50% solution) was added and the stirring continued at 65° C. for an additional 12 hours. The mixture was then allowed to cool to room temperature.

The solid product was filtered off and washed by suspension, stirring for 30 minutes, and filtration from the following fluids:

1. 1 L 2 M NaCl (aqueous)
2. 1 L 2 M NaCl (aqueous)
3. 1 L deionized water repeated until solution conductivity is less than 1 mS/cm The solid was then dried in a 60° C. forced air drying oven to yield 15.7 grams of an off-white solid. The solid was ground and passed through an 80 mesh sieve.

Equivalents

Those skilled in the art will recognize, or be able to ascertain using no more than routine experimentation, many equivalents to specific embodiments of the invention described specifically herein. Such equivalents are intended to be encompassed in the scope of the following claims.

We claim:

1. A method for binding bile salts in a mammal, comprising the step of orally administering to the mammal a therapeutic amount of a hydrocarbon amine polymer having a substituent bound to an amine of the hydrocarbon amine polymer, the substituent including a quaternary amine-containing moiety that is bound to said amine of the hydrocarbon amine polymer by an alkylene linking group having three or more carbons, said quarternary amine-containing moiety also including at least one terminal hydrophobic alkyl substituent, having between about 6 and 20 carbons.

2. The method of claim 1, wherein said orally-administered hydrocarbon amine polymer is crosslinked by a crosslinking moiety.

3. The method of claim 2, wherein said orally-administered hydrocarbon amine polymer is formed by a method that includes crosslinking the hydrocarbon amine polymer by said crosslinking moiety and subsequently adding the substituent, said substituent including a quaternary amine-containing moiety, to said hydrocarbon amine polymer.

4. The method of claim 3, wherein said crosslinking moiety is present in an amount in a range of between about 0.5 and about twenty percent of amines of the orally-administered hydrocarbon amine polymer.

5. The method of claim 4, wherein the crosslinking moiety is present in an amount in a range of between about 0.5 and about six percent of amines of the orally-administered hydrocarbon amine polymer.

6. The method of claim 4, wherein said terminal hydrophobic alkyl substituent includes a beryl group.

7. The method of claim 4, wherein said terminal hydrophobic alkyl substituent includes an octyl group.

8. The method of claim 4, wherein said terminal hydrophobic alkyl substituent includes a decyl group.

9. The method of claim 4, wherein said terminal hydrophobic alkyl substituent includes a dodecyl group.

10. A method for reducing blood cholesterol in a mammal, comprising the step of orally administering to the mammal a therapeutic amount of a hydrocarbon amine polymer having a substituent bound to an amine of the hydrocarbon amine polymer, the substituent including a quaternary amine-containing moiety that is bound to said amine of the hydrocarbon amine polymer by an alkylene linking group having three or more carbons, said quaternary amine-containing moiety also including at least one terminal hydrophobic alkyl substituent, having between about 6 and 20 carbons.

11. A method for treating atherosclerosis in a mammal, comprising the step of orally administering to the mammal a therapeutic amount of a hydrocarbon amine polymer having a substituent bound to an amine of the hydrocarbon amine polymer, the substituent including a quaternary amine-containing moiety that is bound to said amine of the hydrocarbon amine polymer by an alkylene linking group having three or more carbons, said quaternary amine-containing moiety also including at least one terminal hydrophobic alkyl substituent, having between about 6 and 20 carbons.

12. A method for treating hypercholesterolemia in a mammal, comprising the step of orally administering to the mammal a therapeutic amount of a hydrocarbon amine polymer having a substituent bound to an amine of the hydrocarbon amine polymer, the substituent including a quaternary amine-containing moiety that is bound to said amine of the hydrocarbon amine polymer by an alkylene linking group having three or more carbons, said quaternary amine-containing moiety also including at least one terminal hydrophobic alkyl substituent, having between about 6 and 20 carbons.

13. A method for binding bile salts in a mammal, comprising the step of orally administering to the mammal a therapeutic amount of a poly(allylamine) polymer having a substituent bound to an amine of the poly(allylamine), the substituent including a quaternary amine-containing moiety that is bound to said amine of the poly(allylamine) by an alkylene linking group having three or more carbons, said quaternary amine-containing moiety also including at least one terminal hydrophobic alkyl substituent, having between about 6 and 20 carbons.

14. A method for reducing blood cholesterol in a mammal, comprising the step of orally administering to the mammal a therapeutic amount of a poly(allylamine) polymer having a substituent bound to an amine of the poly(allylamine), the substituent including a quaternary amine-containing moiety that is bound to said amine of the poly(allylamine) by an alkylene linking group having three or more carbons, said quaternary amine-containing moiety also including at least one terminal hydrophobic alkyl substituent, having between about 6 and 20 carbons.

15. A method for treating atherosclerosis in a mammal, comprising the step of orally administering to the mammal a therapeutic amount of a poly(allylamine) polymer having a substituent bound to an amine of the poly(allylamine), the substituent including a quaternary amine-containing moiety that is bound to said amine of the poly(allylamine) by an alkylene linking group having three or more carbons, said quaternary amine-containing moiety also including at least one terminal hydrophobic alkyl substituent, having between about 6 and 20 carbons.

16. A method for treating hypercholesterolemia in a mammal, comprising the step of orally administering to the mammal a therapeutic amount of a poly(allylamine) polymer having a substituent bound to an amine of the poly(allylamine), the substituent including a quaternary amine-containing moiety that is bound to said amine of the poly(allylamine) by an alkylene linking group having three or more carbons, said quaternary amine-containing moiety also including at least one terminal hydrophobic alkyl substituent, having between about 6 and 20 carbons.

17. A method for reducing plasma lipid content of a mammal, comprising the step of orally administering to the mammal a therapeutically effective amount of a hydrocarbon amine polymer, comprising a substituent bound to an amine of the hydrocarbon amine polymer, the substituent including a quaternary amine-containing moiety that is bound to said amine of the hydrocarbon amine polymer by an alkylen linking group having three or more carbons, said quaternary amine-containing moiety also including at least one terminal hydrophobic alkyl substituent, having between about 6 and 20 carbons that sequesters with high affinity conjugated primary bile acids including conjugated cholic acid and conjugated chenodeoxycholic acid secreted by said mammal, whereby a substantial portion of said conjugated primary bile acids are excreted by the mammal, thereby causing accelerated lipid metabolism and consequent lowering of plasma lipid content of said mammal.

* * * * *

UNITED STATES PATENT AND TRADEMARK OFFICE
CERTIFICATE OF CORRECTION

PATENT NO.   : 5,618,530
DATED        : April 8, 1997
INVENTOR(S)  : W. Harry Mandeville, III, Stephen Randall Holmes-Farley and John S. Petersen It is certified that error appears in the above-indentified patent and that said Letters Patent is hereby corrected as shown below:

In Column 9, line 32:   Before the word "group", delete the word "beryl" and insert therefor --hexyl--.

Signed and Sealed this

Tenth Day of June, 1997

Attest:

BRUCE LEHMAN

Attesting Officer

Commissioner of Patents and Trademarks